(12) United States Patent
Bodenweber et al.

(10) Patent No.: US 8,717,043 B2
(45) Date of Patent: May 6, 2014

(54) DETERMINING THERMAL INTERFACE MATERIAL (TIM) THICKNESS CHANGE

(75) Inventors: Paul F. Bodenweber, Kingston, NY (US); Virendra R. Jadhav, Farum, NY (US); Kamal K. Sikka, Poughkeepsie, NY (US); Jiantao Zheng, Beacon, NY (US); Jeffrey A. Zitz, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 362 days.

(21) Appl. No.: 13/191,729

(22) Filed: Jul. 27, 2011

(65) Prior Publication Data

US 2013/0027063 A1 Jan. 31, 2013

(51) Int. Cl.
*G01R 27/00* (2006.01)
*G01R 27/26* (2006.01)
*G01N 27/62* (2006.01)
*G01N 27/22* (2006.01)

(52) U.S. Cl.
USPC ............ 324/686; 324/600; 324/671; 324/464

(58) Field of Classification Search
CPC ............ H01L 23/4006; H01L 23/4093; H01L 2023/4062; G01B 7/08
USPC .................................. 324/686, 464, 600, 671
See application file for complete search history.

(56) References Cited

U.S. PATENT DOCUMENTS

| 3,995,696 | A | 12/1976 | Kainer et al. |
| 4,498,043 | A | 2/1985 | Heathcote et al. |
| 6,388,452 | B1 * | 5/2002 | Picciotto ....................... 324/663 |
| 6,829,941 | B2 | 12/2004 | Alexenko et al. |
| 7,451,659 | B2 | 11/2008 | Dallenbach et al. |
| 7,654,159 | B2 | 2/2010 | Enoksson et al. |
| 7,790,511 | B2 | 9/2010 | Chainer |
| 7,798,011 | B2 | 9/2010 | Warren et al. |
| 7,798,723 | B2 * | 9/2010 | Ishii et al. ..................... 384/448 |
| 7,888,792 | B2 | 2/2011 | Chainer |
| 2010/0033935 | A1 * | 2/2010 | Chainer ........................ 361/718 |

FOREIGN PATENT DOCUMENTS

JP 2003023039 A 1/2003

OTHER PUBLICATIONS

Intelligent Multi-Chip-Module (MCM) Package Enhancement, [online]; retrieved on Apr. 1, 2011; retrieved from the Internet http://www.ip.com/pubview/IPCOM000035293D.

* cited by examiner

*Primary Examiner* — Jermele M Hollington
*Assistant Examiner* — Farhana Hoque
(74) *Attorney, Agent, or Firm* — Cantor Colburn LLP; Matthew Zehrer

(57) ABSTRACT

An apparatus for determining a thickness change of thermal interface material (TIM) disposed between first and second elements is provided. The apparatus includes a first part movable with the first element in a movement direction along which the TIM thickness is to be determined, a second part movable with the second element in the movement direction and a sensor to measure a distance between the first and second parts in the movement direction, the measured distance being related to the TIM thickness change.

19 Claims, 3 Drawing Sheets

DETERMINING THERMAL INTERFACE MATERIAL (TIM) THICKNESS CHANGE

BACKGROUND

The present invention relates generally to semiconductor device manufacturing and, more specifically, to an apparatus and method for determining a thermal interface material (TIM) thickness change.

A thermal interface material (TIM) is typically a compliant material with high thermal conductivity that is applied between a heat-generating chip (processor) and a heat spreader (lid) in an electronic package. During operation of the chip, the generated heat is transferred from the chip, through the TIM and into the heat spreader so that a temperature of the chip can be maintained at or below a predetermined level. With this construction, it is seen that a relatively thin TIM bond line provides for good thermal performance but that some minimally thick TIM bond line should be maintained to prevent overloading of the chip.

During assembly processes of electronic packages, thermal degradation usually occurs as a result of TIM bond line thickness changes. However, in situ monitoring of the TIM bond line changes during assembly actual applications is not currently possible.

SUMMARY

According to an aspect of the present invention, an apparatus for determining a thickness change of thermal interface material (TIM) disposed between first and second elements is provided. The apparatus includes a first part movable with the first element in a movement direction along which the TIM thickness change is to be determined, a second part movable with the second element in the movement direction and a sensor to measure a distance between the first and second parts in the movement direction, the measured distance being related to the TIM thickness change.

According to another aspect of the present invention, an apparatus for determining a thickness change of thermal interface material (TIM) disposed between a lid and a processor is provided. The apparatus includes a cap affixed to and movable with the lid in a movement direction along which the TIM thickness change is to be determined, a spring disposed in contact with the cap, a pin disposed to extend through the lid and urged by the spring toward the processor, the pin being thereby movable with the processor in the movement direction and a sensor to measure a distance between the cap and the pin in the movement direction, the measured distance being related to the TIM thickness variation.

According to yet another aspect of the invention, a method for determining a thickness change of thermal interface material (TIM) disposed between a lid and a processor is provided. The method includes machining a through-hole in the lid, disposing in the through-hole a sensor assembly apparatus including a cap movable with the lid and a pin movable with the processor and operating the sensor assembly apparatus to measure a distance between the cap and the pin, the measured distance being related to the TIM thickness change.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Figure 1:
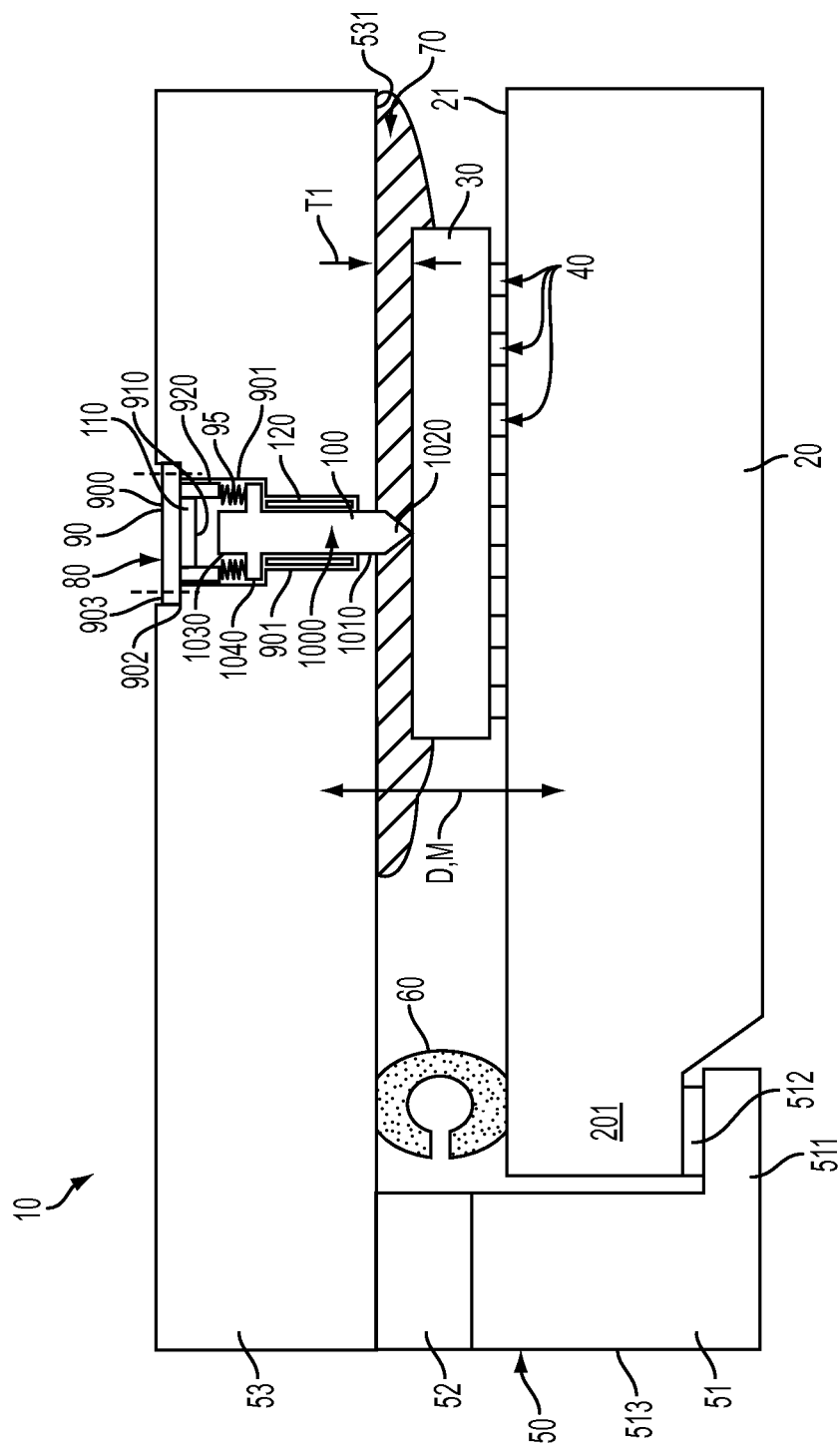
FIG. 1 is a schematic side view of an electronic package.

With reference now to FIG. 1, an electronic package 10 is provided. The electronic package includes a substrate 20 and a chip or processor 30. The substrate 20 has a top surface 21 on which electronic leads are arrayed. The processor 30 is disposed above the top surface 21 and electrically communicates with the electronic leads via soldered electrical connections 40. The substrate 20 is disposed within a lid structure 50, which includes a base plate 51, shims 52 and a lid 53, which is made of metallic thermally conductive materials, such as copper. The base plate 51 includes a plate section 511 having an edge on which a cushion 512 is provided and a wall section 513, which is vertically extended from the plate section 511. An outer rim portion 201 of the substrate overlaps with and sits upon the cushion 512. The shims 52 support the lid 53 such that a lower surface 531 of the lid 53 opposes the top surface 21 of the substrate 20 and the processor 30. The shims 52 sit upon an upper edge of the wall section 513 whereby the shims 52 permit vertical movement of the lid 53. The electronic package 10 further includes a compliant part 60, such as a c-ring, that is disposed between the lower surface 531 of the lid 53 and the top surface 21 of the substrate 20 to provide a bias against downward vertical movement of the lid 53 toward the substrate 20.

Thermal interface material (TIM) 70 is provided between the lower surface 531 of the lid 53 and the processor 30. During operation of the electronic package 10, the processor 30 generates heat that is transmitted to the lid 53, which acts as a heat spreader, via the TIM 70 and, in this way, a temperature of the processor 30 can be maintained at or below a predetermined safe operational level. Thus, it is to be understood that a thickness of the TIM 70 in a substantially vertical direction, D, can be a significant factor in the degree of heat transfer between the processor 30 and the lid 53. In particular, the TIM 70 thickness should be relatively thin without being so thin that defects and failures (i.e., processor 30 overloads) occur. With this in mind, aspects of the present invention provide for in situ bond line monitoring of the TIM 70 using, for example, capacitive sensors during module assembly and in field applications.

In accordance with aspects of the invention, a sensor assembly apparatus 80 for determining the TIM 70 thickness between the lid 53 and the processor 30 is provided. The sensor assembly apparatus 80 includes a first part 90, which is movable with the lid 53 (i.e., a first element) in a movement direction, M. The movement direction, M, is aligned with the substantially vertical direction, D, and defines a dimension along which the TIM 70 thickness is to be determined. The sensor assembly apparatus 80 also includes an elastic element 95, a second part 100, which is movable with the processor 30 in the movement direction, M, a sensor 110 and a bushing 120.

The first part 90 may be formed as a cap 900 that is set into a through-hole 901 formed in the lid 53 by, for example, machining The through-hole 901 may include shoulder portions 902 on which cap edges 903 sit. The cap edges 903 may be affixed to the shoulder portions 902 by, for example, solder or welding (see dotted lines). The shoulder portions 902 and a thickness of the cap 900 are designed such that, when the cap 900 is installed with the cap edges 903 affixed to the shoulder portions 902, a plane of a top surface of the cap 900 is recessed from a plane of the top surface of the lid 53. In this way, a load can be applied to the lid 53 but not the cap 900.

The cap 900 includes a plate 910, which may be formed of metallic and/or electrically conductive materials, and sidewalls 920 that extend downwardly. The elastic element 95 is disposed in contact with the lower edge of the sidewalls 920 and may be anchored thereto. The elastic element 95 may be a spring, such as a compression spring, or any other compliant element. In any case, the elastic element 95 is operably interposed between the first part 90 and the second part 100 and is thereby configured to urge the second part 100 to contact the processor 30 (i.e., a second element).

The second part 100 includes a pin 1000, made from, for example, copper, which is oriented to extend substantially in the movement direction, M. The pin 1000 includes a body 1010, a tip 1020 at an end of the body 1010 that contacts the processor 30, a sensor part 1030 provided at the other end of the body 1010 and a flange 1040. The sensor part 1030 may be formed of metallic and/or electrically conductive materials similar to those of the plate 910. The flange 1040 extends radially outwardly from the body 1010. The elastic element 95 applies a bias thereof to the flange 1040.

The bushing 120 is disposed within the through-hole 901 about the pin 1000 and may be formed of, for example, plastic materials. The bushing 120 supports the orientation and movement of the pin 1000 is the movement direction, M, with limited friction.

Figure 2:
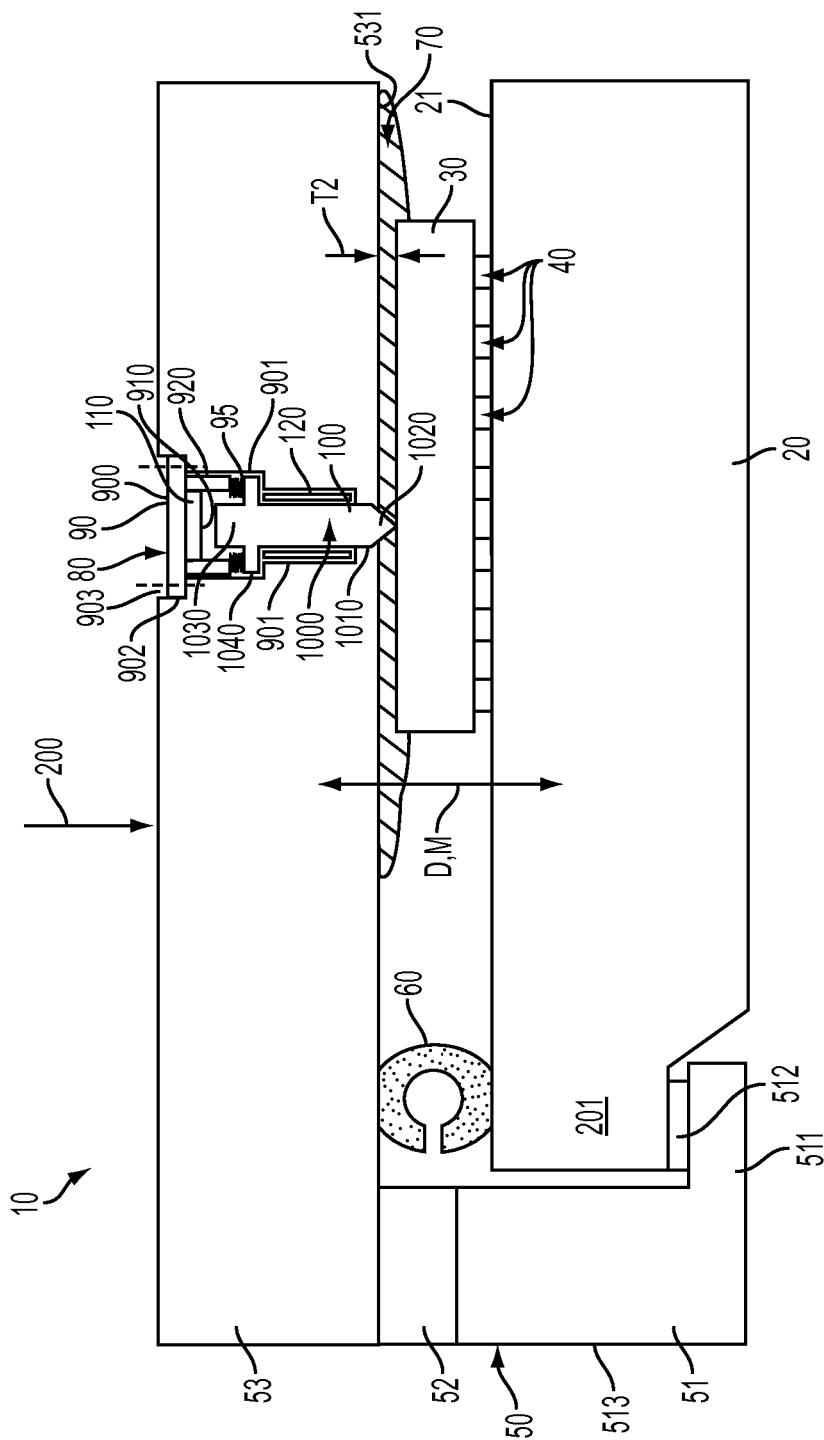
FIG. 2 is a schematic side view of the electronic package of FIG. 1 with a load applied thereto.

With reference to FIGS. 1 and 2, with the configuration described above, it is noted that the TIM 70 is at least initially formed and disposed between the processor 30 and the lid 53 with a predefined first thickness, T1, as shown in FIG. 1. The first thickness, T1, may be approximately 30 microns. At some time thereafter, however, a load 200 may be applied to the lid 53 but not the cap 900, as shown in FIG. 2. This load 200 is substantially larger than the bias applied to the second part 100 by the elastic element 95 and, in fact, may be up to hundreds of pounds per square inch. The load 200 therefore tends to compress the lid structure 50 and thin the TIM 70 toward a second thickness, T2. As mentioned above, it is desirable to have the second thickness, T2, be thin enough to promote good thermal performance but not so thin that the operation of the processor 30 is affected. In accordance with embodiments, the second thickness, T2, may be about 10 microns.

When the load 200 is applied to the lid 53, the lid 53 thins the TIM 70 toward the second thickness, T2, and forces the cap 900 downwardly in the movement direction, M, since the cap 900 is affixed to the lid 53. The pin 1000 meanwhile remains in contact with the processor 30. Thus, as the TIM 70 is thinned, the plate 910 and the sensor part 1030 approach one another in the movement direction, M.

Figure 3:
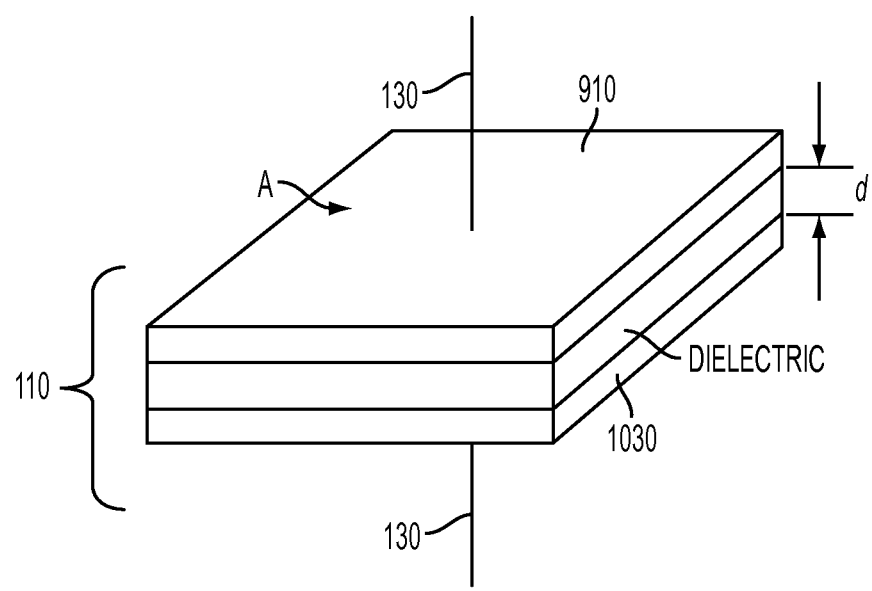
FIG. 3 is a perspective view of a sensor of the electronic package of the FIG. 1.

With reference to FIG. 3 and, in accordance with an embodiment of the invention, the sensor 110 may be a capacitive sensor that includes the plate 910 and the sensor part 1030 as well as leads 130. As shown in FIG. 3, the plate 910 and the sensor part 1030 are each plate-like in appearance and arranged in parallel with one another with a dielectric material interposed between them. As an example, the dielectric material may be air or vacuum space. In either case, a capacitance, C, measured by the sensor 110 is equal to $\in_r * \in_0 * (A/d)$, where $\in_r$ is the relative static permittivity (or dielectric constant) of the material between the plate 910 and the sensor part 1030, $\in_0$ is the electric constant, A is the area of overlap of the plate 910 and the sensor part 1030 and is the separation between the plate 910 and the sensor part 1030 in the movement direction, M.

Thus, it can be seen that the sensor 110 will record an increased capacitance as the TIM 70 thickness decreases. The sensor 110 is thus configured to measure a distance between the first and second parts 90 and 100 in the movement direction, M. In most cases, the measured distance is directly related to the TIM 70 thickness, such that the measured distance provided by the sensor 110 provides a direct indication of the TIM 70 thickness. Often, the relationship between the measured distance and the TIM 70 thickness will be substantially a 1:1 relationship. Where this is not the case due to, for example, part deformation, the non 1:1 relationship may still be known and accounted for by the sensor 110 and/or a computing device coupled to the sensor 110 via the leads 130.

Also, while the sensor 110 is described above as a capacitance sensor, it is understood that the sensor 110 can operate in accordance with multiple other sensing techniques. These include, but are not limited to, optical and/or electro-magnetic sensing techniques. Moreover, while the capacitance sensing described above provides a direct linear measurement of the distance between the cap 900 and the pin 1000, it is understood that other sensing techniques may be employed that would provide measurements that do not have a linear relationship with the distance. In these cases, the non-linear relationship would again be known and accounted for by the sensor 110 and/or a computing device coupled to the sensor 110 via the leads 130.

As described above, the sensor 110 senses the capacitance between the cap 900 and the pin 1000 through a given dielectric material (i.e., air or vacuum space). However, it is to be understood that the sensor 110 can be configured to sense the capacitance through multiple types of media and through media that changes during the loading operation. For example, if the sensor 110 were disposed at an interface between the TIM 70 and the lid 53, it is possible that, during the loading, the dielectric material would include only TIM 70 at an initial time but would include TIM 70 and an additional material at a later time (i.e., air). In these cases, the sensor 110 and/or a computing device coupled to the sensor 110 via the leads 130 may be configured to account for the changing materials as well.

In accordance with further aspects, a method for determining the TIM 70 thickness change is provided and includes machining the through-hole 901 in the lid 53, disposing in the through-hole 901 a sensor assembly apparatus 80 including a cap 900 movable with the lid 53 and a pin 1000 movable with the processor 30 and operating the sensor assembly apparatus 80 to measure a distance between the cap 900 and the pin 1000, the measured distance being related to the TIM 70 thickness variation. In accordance with the method, the disposing may include configuring the sensor assembly apparatus 80 with an elastic element 95, which is disposed in contact with the cap 900 and is configured to urge the pin 1000 toward the processor 30.

The method may further include loading the lid 53 to deform the TIM 70. Here, the operating of the sensor assembly apparatus 80 may be conducted during the loading of the lid 53 such that the deformation can be monitored and stopped when a predefined second thickness, T2, of the TIM 70 is attained. As mentioned above, the operating of the sensor assembly apparatus 80 may include capacitance sensing between the cap 900 and the pin 1000.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. An apparatus for determining a thickness change of thermal interface material (TIM) disposed between first and second elements, the apparatus comprising:
   a first part movable with the first element in a movement direction along which the TIM thickness change is to be determined;
   a second part including a body, a tip at an end of the body and a sensor part at another end of the body, second part being disposed to extend through the first element and the TIM such that the tip is disposed in contact with the second element, the second part being urged toward the second element, and the second part being movable with the second element in the movement direction; and
   a sensor to measure a distance between the first part and the sensor part of the second parts in the movement direction, the measured distance being related to the TIM thickness.

2. The apparatus according to claim 1, wherein the first element comprises a lid and the second element comprises a processor.

3. The apparatus according to claim 1, wherein the first part is affixed to the first element.

4. The apparatus according to claim 3, wherein the first part is recessed from a plane of a surface of the first element.

5. The apparatus according to claim 1, further comprising an elastic element interposed between the first and second parts to urge the second part to contact the second element.

6. The apparatus according to claim 5, wherein the elastic element comprises a spring.

7. The apparatus according to claim 1, wherein the second part comprises a pin oriented to extend in the movement direction.

8. The apparatus according to claim 7, further comprising a bushing disposed within the first element through which the pin extends.

9. The apparatus according to claim 1, wherein the sensor comprises a capacitive sensor.

10. The apparatus according to claim 1, wherein the measured distance is related to the TIM thickness by a substantially 1:1 ratio.

11. An apparatus for determining a thickness change of thermal interface material (TIM) disposed between a lid and a processor, the apparatus comprising:
    a cap affixed to and movable with the lid in a movement direction along which the TIM thickness is to be determined;
    a spring disposed in contact with the cap;
    a pin including a body, a tip at an end of the body and a sensor part at another end of the body, the pin being disposed to extend through the lid and the TIM such that the tip is disposed in contact with the processor, the pin being urged by the spring toward the processor, and the pin being thereby movable with the processor in the movement direction; and
    a sensor to measure a distance between the cap and the sensor part of the pin in the movement direction, the measured distance being related to the TIM thickness.

12. The apparatus according to claim 11, wherein a plane of a surface of the cap is recessed from a corresponding plane of a surface of the lid.

13. The apparatus according to claim 11, further comprising a bushing disposed within the lid through which the pin extends.

14. The apparatus according to claim 11, wherein the sensor comprises a capacitive sensor.

15. The apparatus according to claim 11, wherein the measured distance is related to the TIM thickness by a substantially 1:1 ratio.

16. A method for determining a thickness change of thermal interface material (TIM) disposed between a lid and a processor, the method comprising:
    machining a through-hole in the lid;
    disposing in the through-hole a sensor assembly apparatus including a cap movable with the lid, a pin movable with the processor and a spring, the pin including a body, a tip at an end of the body and a sensor part at another end of the body, the disposing comprising disposing the pin to extend through the lid and the TIM such that the tip contacts the processor and using the spring to urge the pin toward the processor; and
    operating the sensor assembly apparatus to measure a distance between the cap and the pin, the measured distance being related to the TIM thickness.

17. The method according to claim 16, further comprising loading the lid to deform the TIM.

18. The method according to claim 16, wherein the operating of the sensor assembly apparatus is conducted during the loading of the lid.

19. The method according to claim 16, wherein the operating of the sensor assembly apparatus comprises capacitance sensing between the cap and the pin.

* * * * *